United States Patent [19]

Sit et al.

[11] Patent Number: 5,176,633
[45] Date of Patent: Jan. 5, 1993

[54] INJECTION SITE PLATFORM

[76] Inventors: James K. Sit, 120 Barrypoint Rd.; William C. Miller, 100 Fairbank Rd., both of Riverside, Ill. 60546

[21] Appl. No.: 750,508
[22] Filed: Aug. 27, 1991
[51] Int. Cl.⁵ ............................................. A61M 37/00
[52] U.S. Cl. .................................... 604/86; 604/263; 604/283
[58] Field of Search ............. 604/83, 86, 93, 174–175, 604/177, 187, 192, 197, 263–264, 280, 283–284, 905

[56] References Cited

U.S. PATENT DOCUMENTS

| | | | |
|---|---|---|---|
| 4,048,995 | 9/1977 | Mittleman | 604/86 |
| 4,048,996 | 9/1977 | Mittleman et al. | 604/86 |
| 4,752,292 | 6/1988 | Lopez et al. | 604/244 |
| 4,840,618 | 6/1989 | Marvel | 604/187 |
| 4,946,445 | 8/1990 | Lynn | 604/192 |
| 4,964,855 | 10/1990 | Todd et al. | 604/283 |
| 4,981,469 | 1/1991 | Whitehouse et al. | 604/86 |
| 4,986,816 | 1/1991 | Steiner et al. | 604/192 |
| 5,069,666 | 12/1991 | Gericke | 604/86 |
| 5,088,984 | 2/1992 | Fields | 604/167 |

Primary Examiner—C. Fred Rosenbaum
Assistant Examiner—C. Maglione
Attorney, Agent, or Firm—Kinzer, Plyer, Dorn, McEachran & Jambor

[57] ABSTRACT

An injection site platform for use in adding a needle-injected medication to a parenteral fluid being provided to a patient includes a base which has an outlet port of a size and shape to receive a needle-piercible resealable diaphragm. The platform consists of the base member and a port member and when these two elements are assembled together they apply a compressive holding force on the needle-piercible resealable diaphragm. The platform includes one or more sockets which are of a size and shape to hold a hypodermic needle sheath. The sockets each include a plurality of arms which are flexible so that the socket may hold difference size and shape needle sheaths.

14 Claims, 2 Drawing Sheets

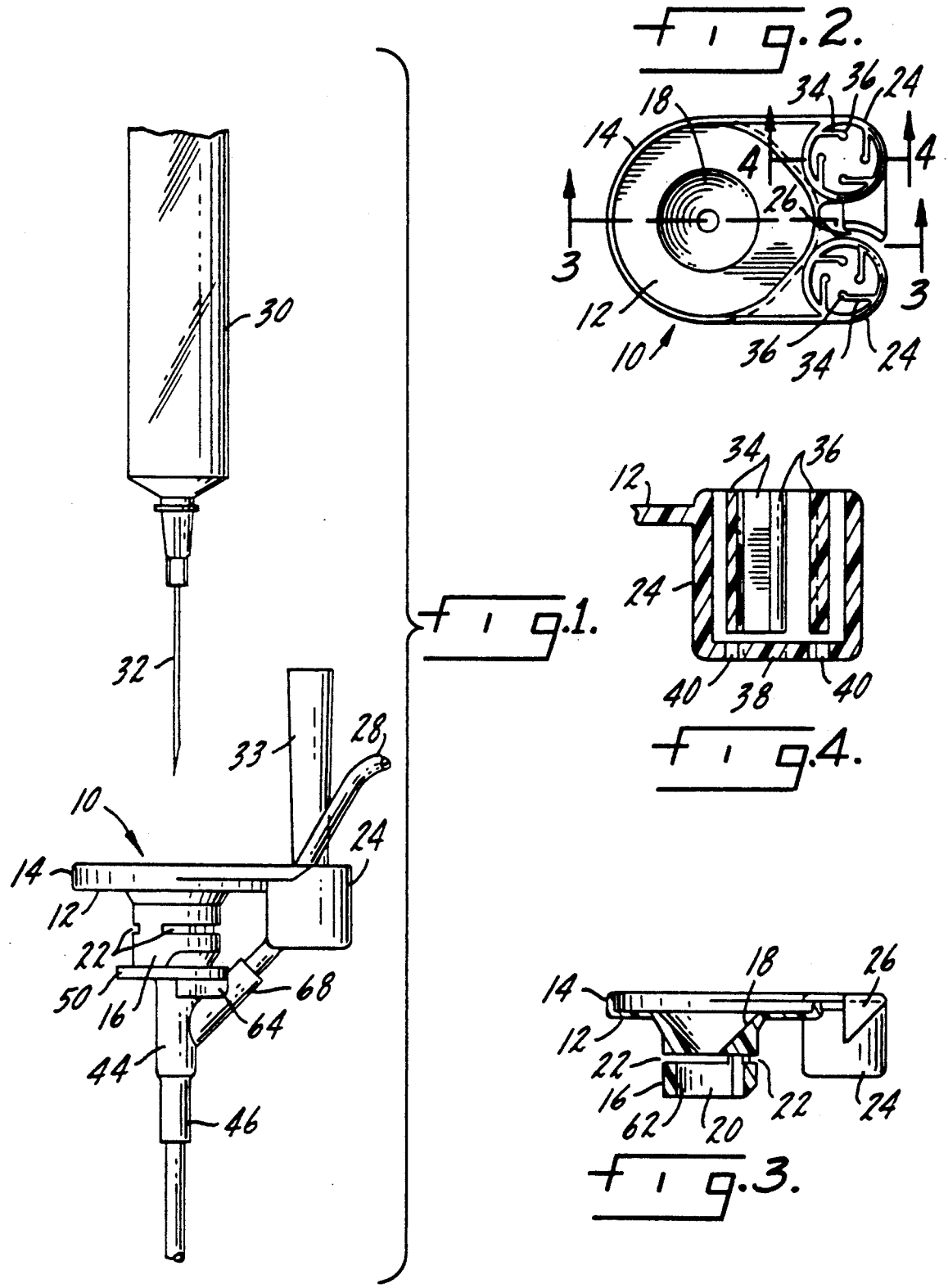

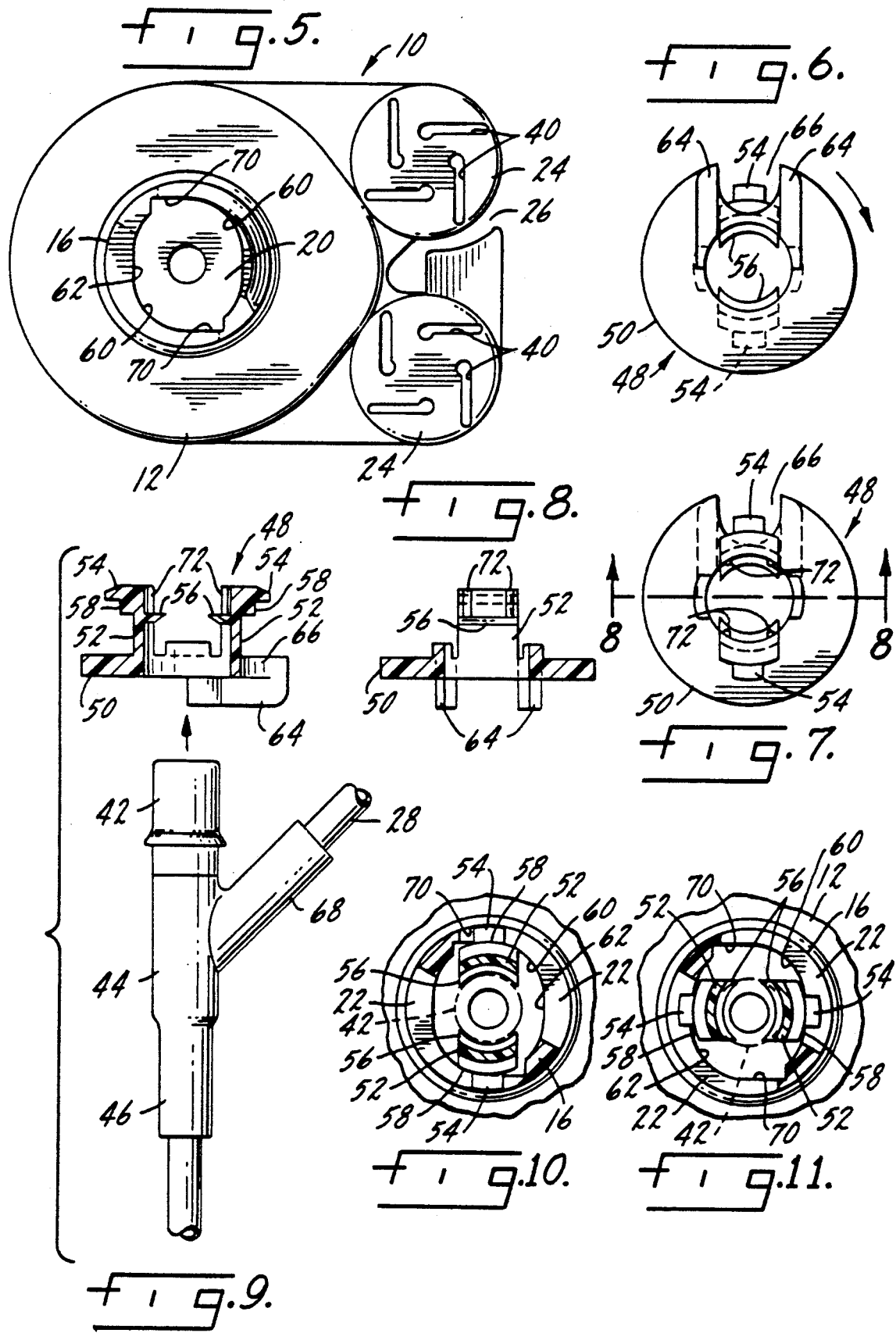

5,176,633

INJECTION SITE PLATFORM

THE FIELD OF THE INVENTION

The present invention relates to an injection site platform for use in adding a needle-injected medication to a parenteral fluid being provided to a patient and is particularly concerned with an improved platform which insures a secure mounting for a needle-piercible resealable diaphragm and to an improved socket for holding the sheath of the hypodermic needle.

DESCRIPTION OF THE RELATED ART

U.S. Pat. No. 4,966,582, an invention of the same inventive entity as herein, discloses an injection site platform. The present invention is an improvement on the '582 patent in the areas of the socket which holds the sheath for the hypodermic needle and the structure that secures the needle-piercible resealable diaphragm to the platform.

SUMMARY OF THE INVENTION

The present invention relates to an injection site platform for use in adding a needle-injected medication to a parenteral fluid being provided to a patient and is particularly concerned with improvements on the platform shown in U.S. Pat. No. 4,966,582.

One purpose of the invention is to provide an injection site platform as described which includes one or more sockets, each of which is formed and adapted to securely hold the covering sheath of a hypodermic needle.

Another purpose of the invention is a platform as described in which the sockets may hold sheaths of many different sizes.

Another purpose is an injection site platform as described including an improved means for securing a needle-piercible resealable diaphragm to the platform.

Other purposes will appear in the ensuing specification, drawings and claims.

BRIEF DESCRIPTION OF THE DRAWINGS

The invention is illustrated diagrammatically in the following drawings wherein:

FIG. 1 is an exploded view of the injection site platform of the invention showing a hypodermic needle positioned for insertion therein, FIG. 2 is a top plan view of the injection site platform of FIG. 1, FIG. 3 is a section along plane 3—3 of FIG. 2, FIG. 4 is an enlarged section along plane 4—4 of FIG. 2, FIG. 5 is an enlarged bottom view of the injection site platform, FIG. 6 is a bottom plan view of the port member forming a part of the platform, FIG. 7 is a top view of the port member, FIG. 8 is a section along plane 8—8 of FIG. 7, FIG. 9 is a side view, similar to FIG. 1, but showing the needle piercible resealable diaphragm in position for insertion within the port member, FIG. 10 is a bottom view showing the port member inserted into the platform, and FIG. 11 is a bottom view, similar to FIG. 10, but showing the port member after it has been turned relative to the platform for securing it therein.

DESCRIPTION OF THE PREFERRED EMBODIMENT

An injection site platform is used to add a needle-injected medication to a parenteral fluid which normally is provided intravenously to a patient. The injection site platform of the present invention eliminates the hazard which can result when doctors or nurses inject medication into an intravenous tube in that the invention not only provides a guide for insuring that the needle will be directed toward the resealable diaphragm forming a part of the intravenous fluid apparatus, but also insures that the sheath covering the needle may be removed and replaced without the danger of the needle piercing the hands of the person using it.

The injection site platform is indicated generally at 10 and includes a base 12 having an upstanding peripheral wall 14. Base 12 has a cylindrical portion 16 including a conical passage 18, the upper end of which terminates at the top of base 12 and the lower end of which opens into a cylindrical passage 20. The cylindrical portion 16 has a pair of oppositely-disposed arcuately-extending slots 22 for use in attaching a port member as will be described hereinafter.

Base 12 includes two spaced integral sockets 24, the upper ends of which merge with peripheral wall 14. Between the two sockets is an opening 26 through which a tube 28 extends, the tube being of the type used to intravenously feed a parenteral fluid to a patient. When it is desired to insert a needle-injected medication, for example from a syringe 30 having a needle 32, once the sheath 33 of the needle has been removed, and the needle is positioned for insertion into the resealable diaphragm, the tube 28 can be constricted against a portion of base 12 bordering opening 26.

Each of the sockets 24 has a plurality of inwardly-directed arms or fins 34 which are integral with the interior wall of the sockets. Each arm 34 terminates in an axially-extending enlarged area 36 and, as clearly shown in FIG. 4, each of the arms stops short of the bottom 38 of the socket. Thus, the only attachment of the arms to the socket is the axial integral connection of the arms with the interior wall of the socket. The arms are thus quite flexible and can accommodate many different sizes and shapes of hypodermic needle sheaths. As shown in FIG. 5, the bottom 38 of each socket has openings 40 which are in alignment with and generally of the same size and shape as the arms 34.

In use, a hypodermic needle and its covering sheath will be inserted into the socket and the sheath will be gripped by the arms 34. The needle and syringe can then be removed and utilized in the normal manner. After the medication from the syringe has been inserted into the intravenous feeding system, the needle may be recovered by placing it into the sheath which has been held by the socket. It is particularly advantageous to have a socket construction as shown, as the non-radially extending arms, which are flexibly joined to the interior wall of the socket, can accommodate many different sizes and shapes of needle sheaths.

The needle-piercible resealable diaphragm is indicated at 42 and is on the upper end of an injection port cap 44 which has an outlet 46. The injection port cap and diaphragm 42, in use, will be inserted into the bottom of a port member 48 which in turn is mounted to the underside of base 12.

The port member which defines the port for the resealable diaphragm 42, and which port is accessible through the conical passage 18 of the base, has a flange 50 and two arcuate upstanding oppositely-disposed flexible arms 52. Each of the arms 52 has an outwardly-extending lug 54 and an inwardly-directed projection 56. Beneath lugs 54 are cam surfaces 58 which cooperate with cam surfaces 60 on the interior cylindrical wall 62 of the cylindrical portion 16 of the base. The port member may include a pair of spaced guides 64 which define a slot 66 for the portion 68 of injection port cap 44. Each of the arms also include axial projections 72 for use in gripping the injection port cap.

Looking specifically at FIGS. 10 and 11, the interior surface 62 of the base 12 has a pair of oppositely-disposed axial recesses 70 which are formed and adapted to accommodate lugs 54 when the port member is axially inserted into the base. In such assembly, the port member may first be positioned over the resealable diaphragm 42, with the arms 52 positioned on either side, after which the lugs 54 of the port member will be aligned with recesses 70 and the port member will be pushed into the base until the lugs are aligned with the arcuate slots 22. The port member is then twisted clockwise until the cam surface 58 directly beneath each lug 54 is in contact with a cam surface 60 on the cylindrical portion 16 of base 12. The camming action between these two surfaces has the effect of forcing the flexible arms inward so that they tightly grip the resealable diaphragm 42. Note the difference between the shape of the diaphragm as shown in FIG. 10, prior to twisting of the port member, and the shape of the diaphragm in FIG. 11, after twisting, in which the arms are shown to be compressed into the exterior of the diaphragm. The interior of the arms 52 have inwardly-directed projections 56 and 72 which will bite into the exterior of the resealable diaphragm, thus securing it to the port member which itself has been attached to the base.

When it is desired to inject a medicine from a syringe into the intravenous line, the needle sheath is first removed by use of one of the sockets as shown and described above, the tube 28 may be fully or partially constricted by pressing it against the side of opening 26 and then the needle 32 may pierce the resealable diaphragm. After the medication has been injected, the constriction of tube 28 may be released and the needle sheath may be retrieved from the socket.

Of particular advantage is the mechanism for holding the resealable diaphragm to the injection site platform. The arms have interior projections which bite into the exterior of the resealable diaphragm, as the arms are compressed during assembly of the injection site platform. Further, the particular construction of the sockets permits a wide variety of sizes and shapes of needle sheaths to be removed and held while the medication is being injected.

Whereas the preferred form of the invention has been shown and described herein, it should be realized that there may be many modifications substitutions and alterations thereto.

The embodiments of the invention in which an exclusive property or privilege is claimed are defined as follows:

1. An injection site platform for use in adding a needle-injected medication to a parenteral fluid being provided to a patient, said platform including a base, an opening in said base outlet port means of a size and shape to receive a needle-piercible resealable diaphragm, said outlet port means having means for compressively holding injection port caps having resealable diaphragms, a conical wall with the smaller portion thereof adjoining said outlet port means and the larger diameter portion thereof being connected to and terminating at said base aligning said opening with said outlet port means, a portion of said platform providing a surface against which a tube carrying parenteral fluid may be manually constricted to limit the flow therethrough, at least one socket in said base of a size and shape to receive the sheath covering a hypodermic needle, whereby a syringe and needle covered by the sheath may be placed in the socket, the socket gripping the sheath to permit removal of the syringe and needle for use in adding a needle-injected medication to the parenteral fluid, the improvement comprising a plurality of inwardly-directed flexible members positioned in each socket for releasably gripping a needle sheath.

2. The injection site platform of claim 1 further characterized in that said flexible members are non-radially extending arms attached to an interior socket wall.

3. The injection site platform of claim 2 further characterized in that said arms extend substantially the depth of a socket and are only attached to the socket along the socket interior wall.

4. The injection site platform of claim 3 further characterized in that each of said flexible arms terminates in an enlarged area.

5. The injection site platform of claim 1 further characterized in that there are a pair of sockets and an opening in said platform between said sockets, said opening providing the surface against which a tube carrying parenteral fluid may be manually constricted.

6. The injection site platform of claim 1 further characterized in that said outlet port means is formed by a port member releasably attached to said base.

7. The injection site platform of claim 6 further characterized in that said port member is rotatably attached to said base.

8. An injection site platform for use in adding a needle-injected medication to a parenteral fluid being provided to a patient, said platform including a base, an opening in said base, an outlet port member secured to said base in alignment with said opening and having an outlet port of a size and shape to receive a needle-piercible resealable diaphragm, said port member being releasably secured to said base, said base having a cam surface, attaching said port member to said base causing said cam surface to apply an inwardly-directed force to said port to reduce the interior diameter thereof to apply a compressive force to the resealable diaphragm positioned therein.

9. The injection site platform of claim 8 further characterized in that said base and port member have cooperating interlocking surfaces.

10. The injection site platform of claim 9 further characterized in that said base has spaced arcuate openings, said port member having spaced outwardly-directed lugs, the lugs on said port member being received within the openings on said base.

11. The injection site platform of claim 8 further characterized in that said port member has a cam surface for engagement with the cam surface on the base.

12. The injection site platform of claim 11 further characterized in that said port member ha oppositely-disposed arcuate arms which define the outlet port, spaced arcuate openings in said base, said arms having outwardly-directed lugs which interlock with said spaced arcuate openings in the base to attach the port member to the base.

13. The injection site platform of claim 12 further characterized in that said base includes a cylindrical portion, said openings being within said cylindrical portion, said cylindrical portion including axially extending recesses to receive said lugs for insertion of said port member into the cylindrical portion of said base.

14. The injection site platform of claim 13 further characterized in that each of the recesses in the cylindrical portion terminate in a cylindrical portion opening, relative rotary movement between the port member and the cylindrical portion of the base causing the cam surfaces on said port member and base to constrict the port opening in said port member.

* * * * *